(12) United States Patent
Pedicini et al.

(10) Patent No.: US 12,257,688 B2
(45) Date of Patent: Mar. 25, 2025

(54) ORTHOPEDIC ROTARY TOOL WITH REDUCED REACTIONARY TORQUE

(71) Applicant: Fidelis Partners, LLC, Cheyenne, WY (US)

(72) Inventors: Christopher Pedicini, Brentwood, TN (US); Joshua Pedicini, Nashville, TN (US)

(73) Assignee: FIDELIS PARTNERS, LLC, Cheyenne, WY (US)

( * ) Notice: Subject to any disclaimer, the term of this patent is extended or adjusted under 35 U.S.C. 154(b) by 0 days.

(21) Appl. No.: 18/531,784

(22) Filed: Dec. 7, 2023

(65) Prior Publication Data

US 2024/0188984 A1  Jun. 13, 2024

Related U.S. Application Data

(60) Provisional application No. 63/459,815, filed on Apr. 17, 2023, provisional application No. 63/447,199, filed on Feb. 21, 2023, provisional application No. 63/439,681, filed on Jan. 18, 2023, provisional application No. 63/431,192, filed on Dec. 8, 2022.

(51) Int. Cl.
| | |
|---|---|
| *B25F 5/00* | (2006.01) |
| *A61B 17/00* | (2006.01) |
| *A61B 17/16* | (2006.01) |
| *A61B 17/3207* | (2006.01) |

(52) U.S. Cl.
CPC .......... *B25F 5/001* (2013.01); *A61B 17/1626* (2013.01); *A61B 17/1628* (2013.01); *A61B 17/1631* (2013.01); *A61B 17/320758* (2013.01); *A61B 2017/00398* (2013.01)

(58) Field of Classification Search
CPC . B25F 5/001; A61B 17/1626; A61B 17/1628; A61B 17/1631; A61B 17/320758; A61B 2017/00398
See application file for complete search history.

(56) References Cited

U.S. PATENT DOCUMENTS

| | | | |
|---|---|---|---|
| 6,889,778 B2 * | 5/2005 | Colangelo, III | ........ B25B 21/02 173/93.5 |
| 2008/0099217 A1 * | 5/2008 | Seith | ...................... B25B 21/026 173/1 |
| 2018/0029205 A1 * | 2/2018 | Livingston | .............. B25B 21/02 |

* cited by examiner

*Primary Examiner* — Kevin T Truong
*Assistant Examiner* — Diana Jones
(74) *Attorney, Agent, or Firm* — XSENSUS LLP

(57) ABSTRACT

An orthopedic rotary tool may include a motor, a first clutch, a first drive path, a second drive path, a second clutch, a rotating mass, and an output anvil. The orthopedic rotary tool may drive, by the motor and the first clutch, a first drive path that causes the output anvil to rotate at a speed. The orthopedic rotary tool may selectively enable, by the motor and the second clutch, a second drive path that causes the rotating mass to engage to the output anvil and increase the speed of the output anvil.

20 Claims, 16 Drawing Sheets

ORTHOPEDIC ROTARY TOOL WITH REDUCED REACTIONARY TORQUE

CROSS-REFERENCE TO RELATED APPLICATIONS

This application claims the benefit of U.S. Provisional Application No. 63/431,192, filed Dec. 8, 2022, U.S. Provisional Application No. 63/439,681, filed Jan. 18, 2023, U.S. Provisional Application No. 63/447,199, filed Feb. 21, 2023, and U.S. Provisional Application No. 63/459,815, filed Apr. 17, 2023, each of which is incorporated herein by reference in its entirety. This application is related to U.S. patent application Ser. No. 18/531,774, filed Dec. 7, 2023, which is incorporated herein by reference in its entirety.

BACKGROUND

Orthopedic rotary tools are used in orthopedic operations, such as orthopedic surgeries, to perform various orthopedic techniques. For example, orthopedic rotary tools can be used to perform orthopedic techniques during joint replacement operations, fracture fixation operations, and/or spinal fusion operations.

SUMMARY

Some implementations described herein relate to an orthopedic rotary tool with reduced reactionary torque. The orthopedic rotary tool may include a motor; a drive shaft operatively coupled to the motor; an output anvil operatively coupled to the drive shaft; a rotating mass; and a clutch operatively coupled to the rotating mass and the anvil, wherein the clutch is configured to engage the rotating mass to the output anvil when the output anvil drops to less than a design speed; and wherein after such engagement the clutch is configured to disengage the rotating mass from the output anvil to allow the rotating mass to reaccelerate.

Some implementations described herein relate to a method for operating an orthopedic rotary tool, the orthopedic rotary tool including a motor, a first clutch, a first drive path, a second drive path, a second clutch, a rotating mass, and an output anvil, the method comprising: driving, by the motor and the first clutch, a first drive path that causes the output anvil to rotate at a speed; and selectively enabling, by the motor and the second clutch, a second drive path that causes the rotating mass to engage to the output anvil and increase the speed of the output anvil.

Some implementations described herein relate to an orthopedic rotary tool including a motor; a first drive path; a first clutch; a second drive path; a second clutch; and an output anvil; wherein the motor is configured to drive the first drive path and the second drive path, and wherein the first drive path is configured to drive the output anvil. It is understood that the first and second drive path may share some elements as they communicate torque from the motor to the anvil.

DETAILED DESCRIPTION OF EXAMPLE EMBODIMENTS

Figure 1:
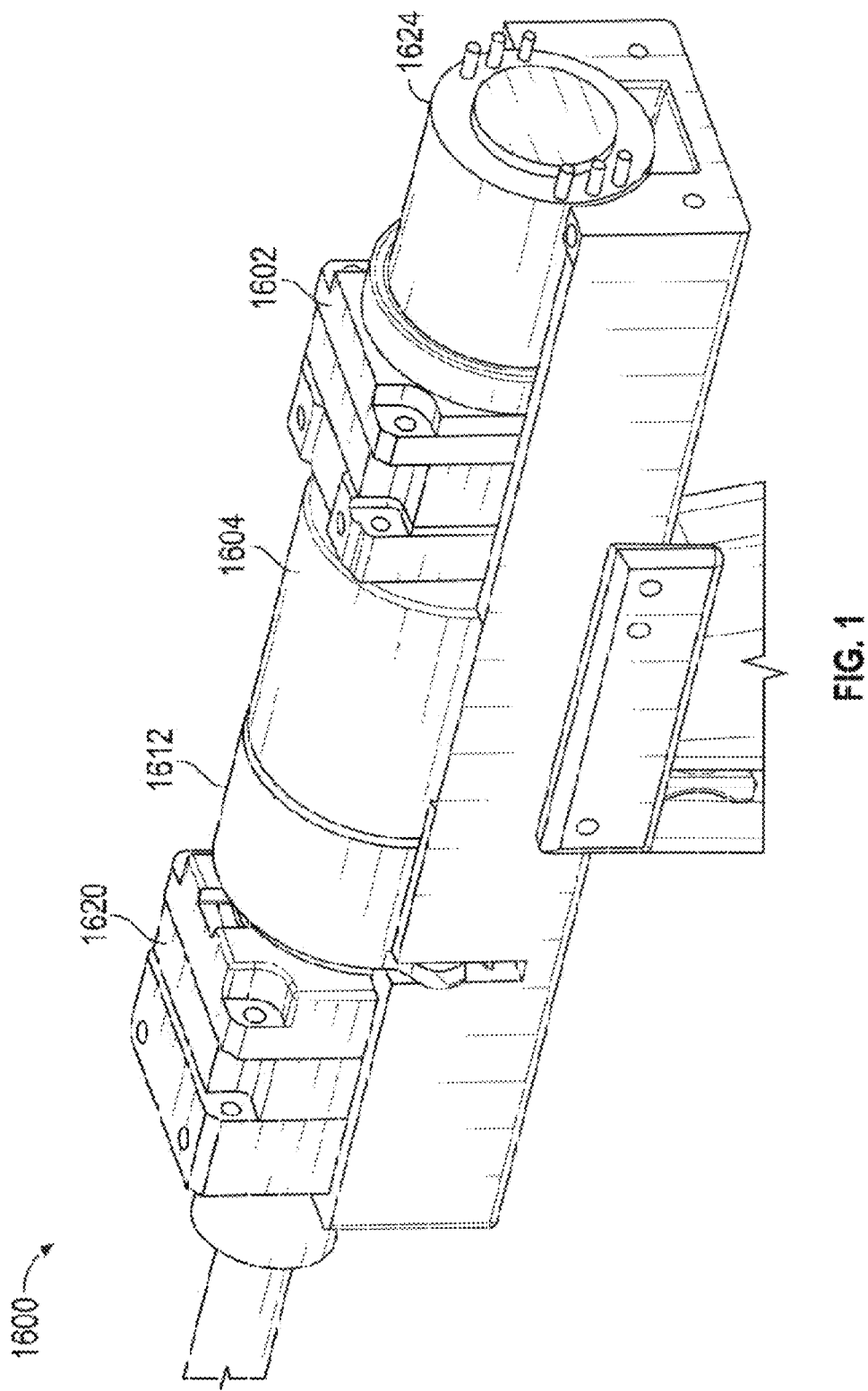
FIG. 1 is a diagram of an example orthopedic rotary tool with reduced reactionary torque.

The following detailed description of example implementations refers to the accompanying drawings. The same reference numbers in different drawings may identify the same or similar elements.

An orthopedic rotary tool (e.g., a reamer, a drill, among other examples) can be used (e.g., by an operator, a surgeon, and/or a robot, among other examples) to perform one or more orthopedic techniques during an orthopedic procedure. For example, the operator may use the orthopedic rotary tool to cut, drill, and/or shape bone during the orthopedic procedure.

To cut, drill, and/or shape the bone during the orthopedic procedure, the operator may cause a component (e.g., edges or cutting flutes of a reamer, among other examples) of the orthopedic rotary tool to rotate and interact with the bone. As an example, the orthopedic rotary tool may include a motor to provide a rotational force that causes the component to rotate. As the component rotates, the operator causes the component to interact with the bone, and the rotational motion, combined with the component, creates a cutting action that removes bone material.

However, during the cutting process, the interaction between the component and the bone generates a reactionary torque (e.g., a reactionary force that opposes rotation of the component). In some cases, a high reactionary torque may be generated which requires the operator of the orthopedic rotary tool to exert a high counteracting force from his wrist to overcome the high reactionary torque and maintain control over movement associated with the orthopedic rotary tool. If the surgeon has to overcome high reactionary torque during orthopedic procedures, this introduces drawbacks and challenges. These include operator fatigue, wrist injury and reduced cutting precision of the orthopedic implement potentially resulting in suboptimal implant positioning and stability. Furthermore, existing techniques employed to mitigate high reactionary torque during orthopedic procedures generate excessive noise levels, which can lead to hearing damage of the operator.

Some implementations described herein relate to an orthopedic rotary tool with reduced reactionary torque. For example, the orthopedic rotary tool may include a motor, a drive shaft operatively coupled to the motor, an output anvil operatively coupled to the drive shaft, a rotating mass (e.g., a flywheel), a clutch operatively coupled to the rotating mass, and a controller. In some implementations, the controller may measure the rotational speed of the output anvil and based on comparison of that speed to a desired speed use a clutch to selectively couple the rotating mass to the output anvil to transmit additional torque from the rotating mass to the output anvil. As an example, if the controller determines that the output rotational speed of the output anvil drops below a threshold rotational speed, then the controller may cause the clutch to selectively couple the rotating mass to the output anvil to transmit additional torque from the rotating mass to the output anvil.

In this way, the orthopedic rotary tool may selectively couple a rotating mass to the output anvil to provide a torque that overcomes a high reactionary torque at the output anvil (e.g., via a clutch that can be mechanically and/or electronically controlled to selectively couple a rotating mass to the output anvil, as described in more detail elsewhere herein.

Figure 2:
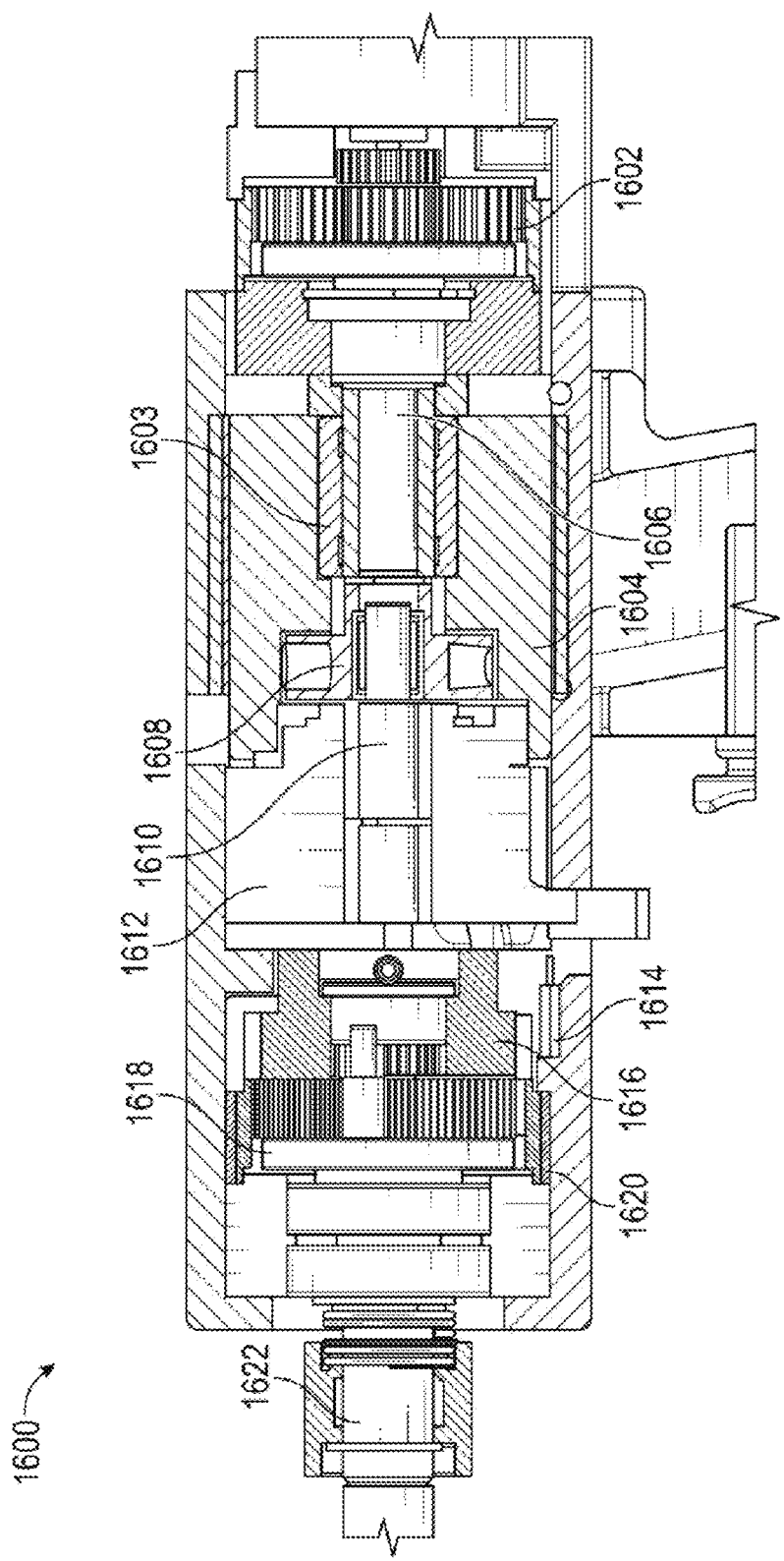
FIG. 2 is a diagrammatical cross-section of the orthopedic rotary tool of FIG. 1.

FIG. 1 is a diagram of an example orthopedic rotary tool 1600 with reduced reactionary torque. FIG. 2 is a diagrammatical cross-section of the orthopedic rotary tool 1600 of FIG. 1. As shown in FIGS. 1-2, the orthopedic rotary tool 1600 includes a primary gear box 1602, a one-way drive bearing 1603, a rotating mass 1604, a drive shaft 1606, a slip clutch 1608, a bypass shaft 1610, an electronic clutch 1612 (e.g., a wrap spring clutch, among other examples), a rotational speed sensor 1614 a carriage plate driver 1616, a gear carrier 1618, a secondary gear box 1620, and an output anvil 1622.

Figure 3:
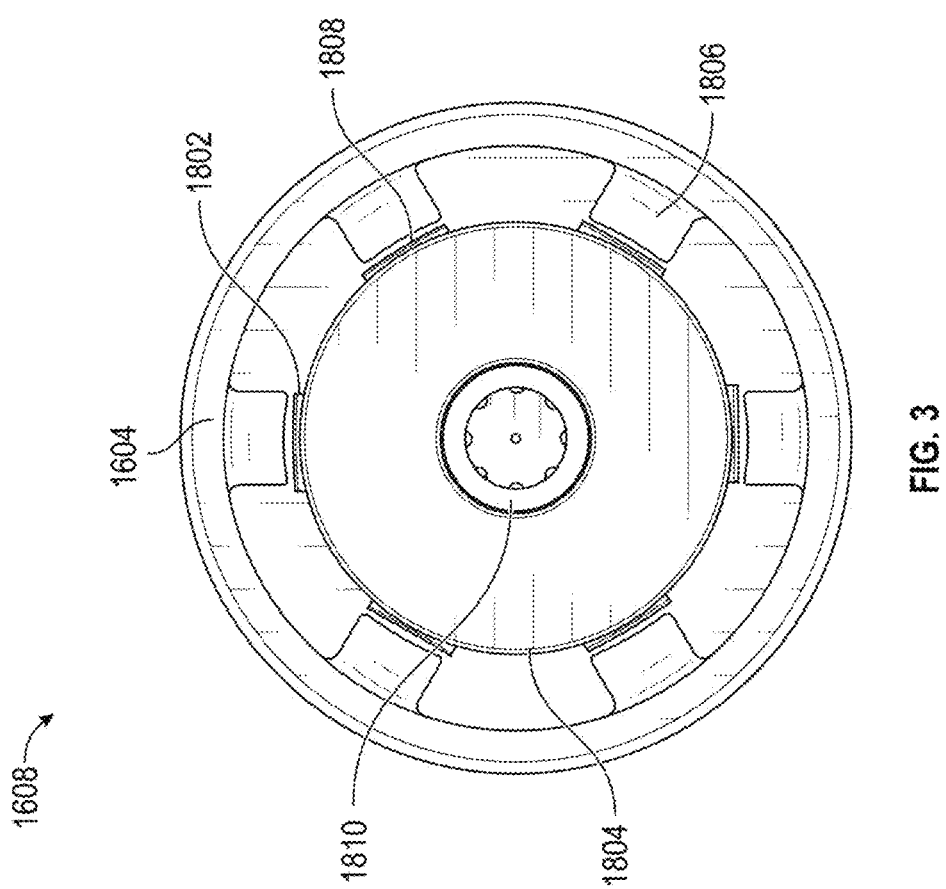
FIG. 3 is a diagram of an example magnetic slip clutch of the orthopedic rotary tool of FIG. 1.
Figure 4:
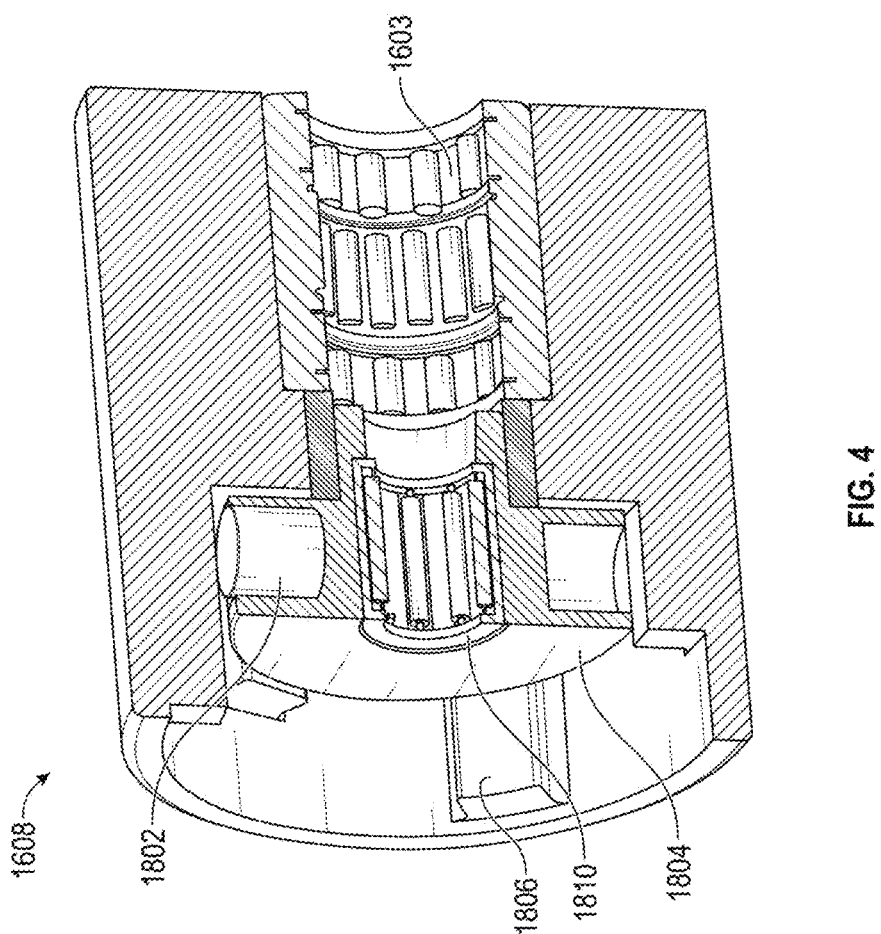
FIG. 4 is a partial diagrammatical cross-section of the magnetic slip clutch of FIG. 3 operatively coupled to an example one-way bearing.
Figure 5:
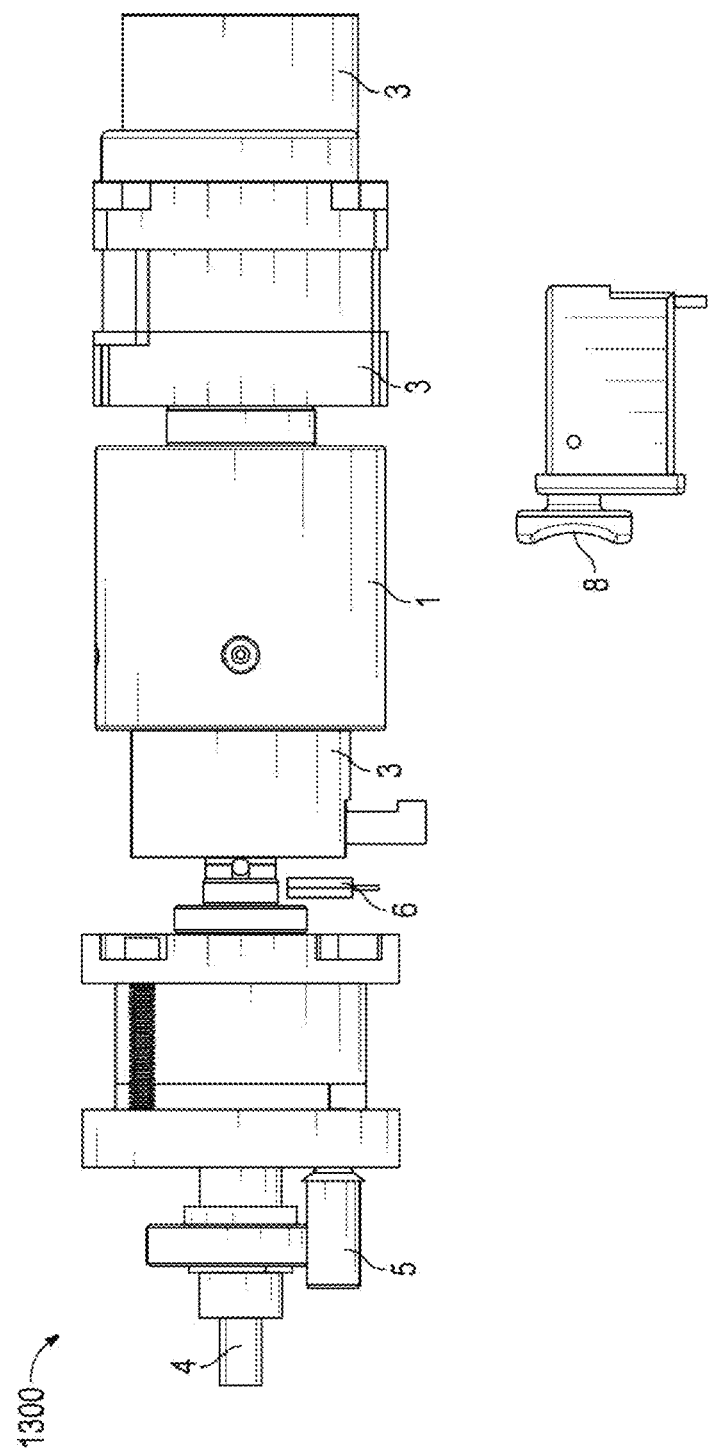
FIG. 5 is a diagram of an example orthopedic rotary tool.
Figure 6:
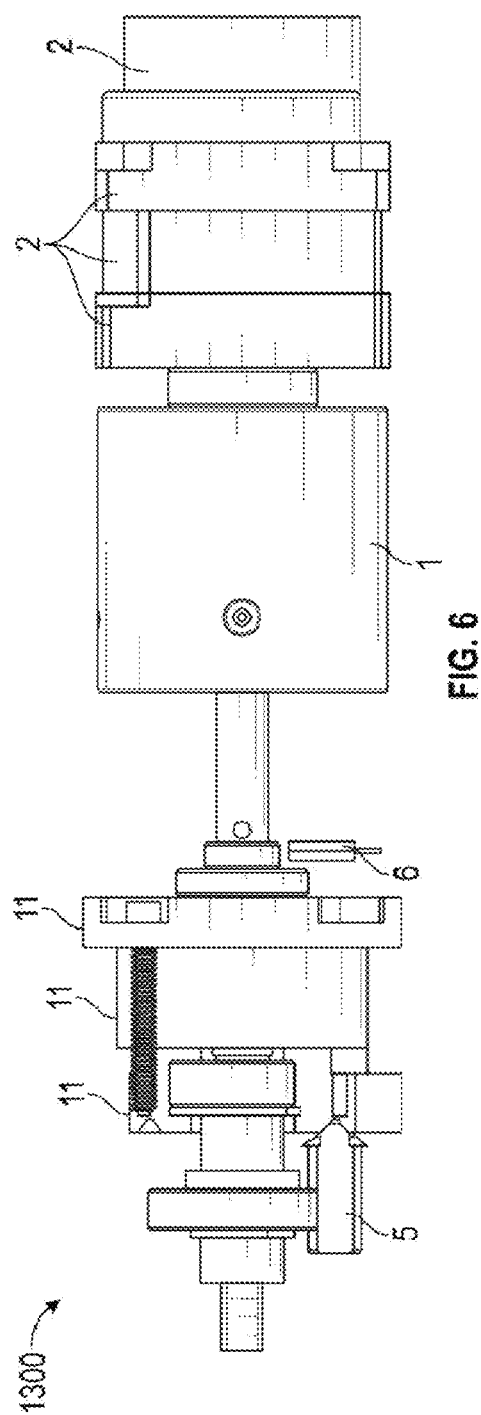
FIG. 6 is a diagram of the orthopedic rotary tool of FIG. 5 and a partial interior view of an example gearbox.
Figure 7:
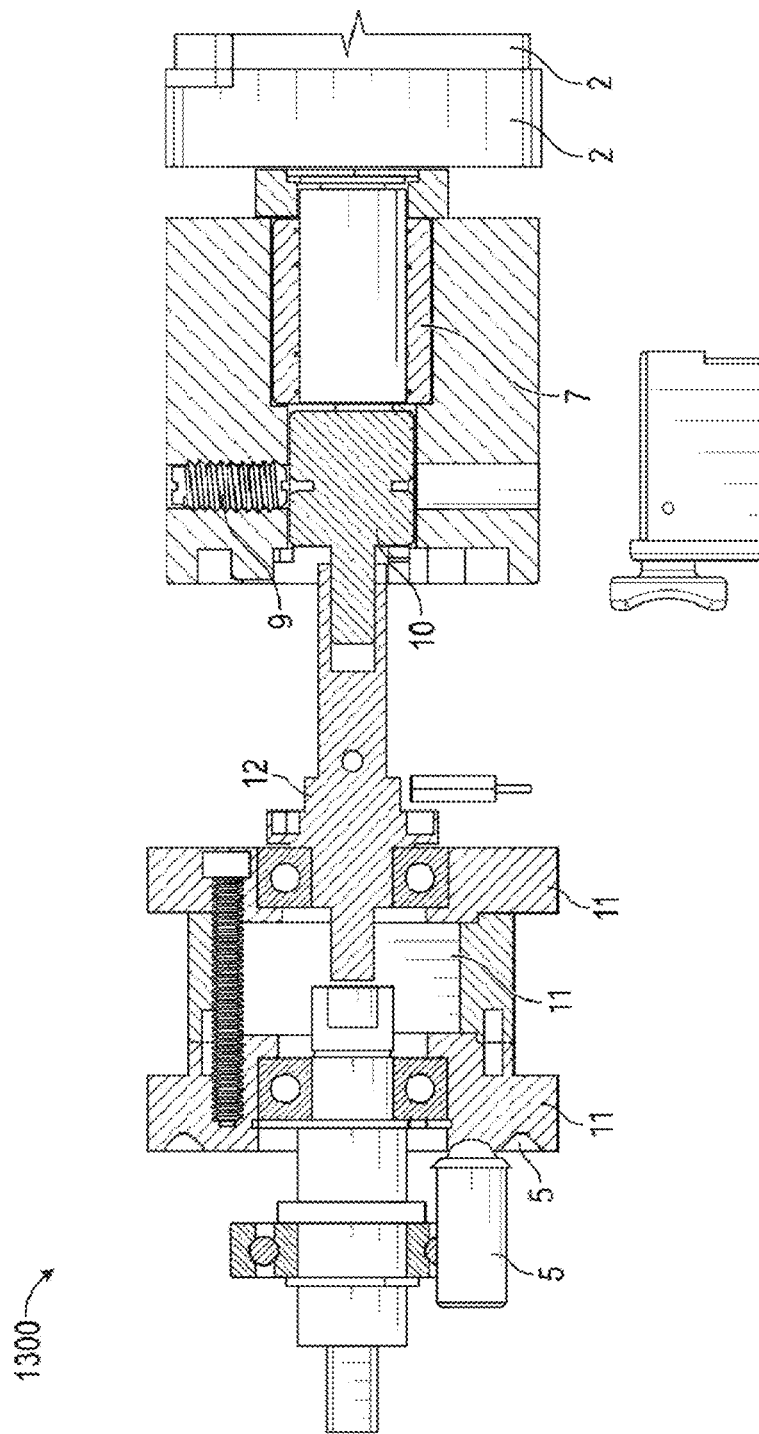
FIG. 7 is a diagrammatical cross-section of the orthopedic rotary tool of FIG. 5.

FIG. 3 is a diagram of a magnetic slip clutch 1608 of the orthopedic rotary tool 1600 of FIG. 1. FIG. 4 is a partial diagrammatical cross-section of the magnetic slip clutch 1608 operatively coupled to the one-way bearing 1603. As shown in FIGS. 3-4, the orthopedic rotary tool 1600 includes magnets 1802, a center drive 1804, splined teeth 1806, an airgap 1808 (e.g., that is positioned between the magnets 1802 and the splined teeth 1806 as shown in FIG. 3), and a bypass shaft overrunning bearing 1810. The bypass shaft overrunning bearing 1810 is used to drive a bypass shaft (such as the bypass shaft 1610 shown in FIG. 2). The bypass shaft is a unique invention that enables the output anvil to be turned at a desired output rpm range and yet allow slippage at a design speed and as a result of said slippage to operatively couple additional torque to the output by using an alternate and parallel path. As an example, a design speed is a speed of the output anvil when the orthopedic rotary tool operates with no (or minimal) load when driven solely by the first drive path.

As further shown in FIG. 3, the magnetic slip clutch 1608 is disposed within the rotating mass 1604. Although the orthopedic rotary tool 1600 is shown and described as having the magnetic slip clutch 1608 disposed within the rotating mass 1604, the orthopedic rotary tool 1600 may utilize any suitable slip or overload clutch, disposed in any suitable position associated with the orthopedic rotary tool 1600.

Although the orthopedic rotary tool 1600 is described as using the magnetic slip clutch 1608, the orthopedic rotary tool 1600 may use any suitable clutch, such as a friction clutch, hysteresis clutch, an eddy current clutch, and/or a spring ball relief clutch, among other examples. Different clutches are associated with different breakaway or slippage characteristics. One important distinction associated with this disclosure is that the bypass shaft rotational energy is operatively communicated from the motor to the anvil through a slip or breakaway clutch in which the torque transmitted to the operator is reduced when the torque reaches a slip torque (e.g., when the torque satisfies a torque threshold). In some implementations, the slippage or breakaway effect could be achieved by controlling or modulating an electrically activated clutch.

Accordingly, the "slip torque" of a clutch is associated with a maximum transmissible torque that may be transmitted before an angular rotation at an input side of the clutch exceeds (e.g., for a period of time) an angular rotation on an output side of the clutch.

In some implementations, an overload torque level (e.g., a torque level at the slip torque) may be approximately 25 inch-pounds (e.g., as measured, by a sensor device of the orthopedic rotary tool 1600, at the output anvil 1622) although a more preferable slippage would be about 10 inch-pounds.

In some implementations, the rotating mass 1604 may be operably coupled to the bypass shaft 1610 via the magnetic slip clutch 1608. The bypass shaft 1610 may pass through a center of the electronic clutch 1612 and may engage a pinion in the secondary gearbox 1620. During normal operation, the bypass shaft 1610 may engage the secondary gear box 1620, which causes the output anvil 1622 to rotate at a design speed (e.g., between an rpm range of 100 and 500 and/or between a range of 280 and 340, among other examples).

In some implementations, if the output anvil 1622 encounters a high torque load (e.g., which causes excessive reactionary torque being transmitted to the operator of the orthopedic rotary tool 1600), then the magnetic slip clutch 1608 may slip (e.g., or begin to slip), which limits the reactionary torque that is transmitted to the operator of the orthopedic rotary tool 1600. In other words, the magnetic slip clutch 1608 may decouple the bypass shaft 1610 and the output anvil from the rotating mass 1604 (e.g., based on slipping). In some implementations, the magnetic slip clutch 1608 may slip based on a slip torque of 2 to 50 inch-pounds.

In this way, the reactionary torque transmitted to the operator of the orthopedic rotary tool 1600 may be limited. In some implementations, if the slip torque is exceeded, then the magnetic slip clutch 1608 slips, which causes a rotational speed associated with the output anvil 1622 to be reduced, temporarily. In other words, when the magnetic slip clutch 1608 slips, the output anvil 1622 slows down or stops based on the anvil torque exceeding the slip torque.

In some implementations, the rotational speed sensor 1614 is a Hall Effect sensor and may monitor the rotational speed of the output anvil 1622. The Hall Effect sensor may send, and a controller (e.g., a control board and/or a control circuit, among other examples) associated with the orthopedic rotary tool 1600 may receive, an indication of the rotational speed of the output anvil 1622. Although the orthopedic rotary tool 1600 is described as using the Hall effect sensor to monitor the rotational speed of the output anvil 1622, the orthopedic rotary tool 1600 may use any suitable technique and/or sensor device to monitor the rotational speed of the output anvil 1622.

In some implementations, the controller may control an electronic clutch 1612, as described in more detail elsewhere herein. Accordingly, the controller may include various semiconductor components including but not limited to transistors, integrated circuits, and passive components such as inductors, capacitors etc.

In some implementations, the controller may cause the electronic clutch 1612 to be engaged based on the rotational speed of the anvil deviating from a design speed. Engaging the electronic clutch 1612 causes the rotating mass 1604 to be operatively coupled to the output anvil 1622, as described in more detail elsewhere herein. Accordingly, for example, engaging the electronic clutch 1612 may increase a torque (e.g., may "boost" the torque) by enabling the rotational inertia of the rotating mass to be coupled to the output anvil.

In some implementations, a frequency and/or duty cycle of the electronic clutch 1612 can be optimized to provide the optimized operating characteristics associated with the orthopedic rotary tool 1600 (e.g., which may be based on operator preferences, orthopedic procedures, and/or orthopedic techniques, among other examples). As an example, the electronic clutch 1612 may be engaged at variable frequencies ranging from a single engagement up to 50 Hz.

In some implementations, the orthopedic rotary tool 1600 may include only the secondary (e.g., auxiliary) drive path (e.g., the orthopedic rotary tool 1600 may not include the bypass shaft 1606). The frequency and/or duty cycle of the electronically activated clutch 1612 may be modulated based on an output rpm sensor to achieve a desired output rpm range. For example, in a no-load condition (e.g., when the orthopedic rotary tool 1600 is operating under no load), if the rpm sensor measures an output rpm of 1000 rpm, then the controller (e.g., based on an indication provided by the rpm sensor) may reduce the duty cycle and/or frequency of the electronic clutch 1612 to decrease the rpm to the desired output rpm range. As another example, under a high-load condition, (e.g., when the orthopedic rotary tool 1600 is operating under a high torque load), if the rpm sensor measures an output rpm of 25 rpm, then the controller (e.g., based on an indication provided by the rpm sensor) may increase the duty cycle and/or frequency of the electronic clutch 1612 to overcome the high torque load and increase the output rpm (e.g., of the output anvil 1622).

In some implementations, the secondary drive path may be associated with engaging the electronic clutch 1612. As an example, if the controller determines that the rotational speed of the output anvil 1622 has dropped below the desired design speed (e.g., when the magnetic slip clutch 1608 slips or begins slipping), then the controller may selectively activate the electronic clutch 1612, which causes the rotating mass to be operatively coupled to the output anvil 1622. Accordingly, a high rotational energy of the rotating mass 1604 may be transmitted to the output anvil 1622 to increase the rpm of the output anvil 1622 towards the desired output rpm range. In other words, the motor 1624 drives the rotating mass 1604, which is then selectively coupled to and decoupled from the output anvil 1622 by the electronically activated clutch 1612.

In some implementations, the electronic clutch 1612 may be "pulsed" (e.g., based on a frequency), which causes the rotating mass 1604 to be repeatedly coupled to, and decoupled from, the output anvil 1622. As an example, the controller may selectively pulse the electronic clutch 1612, which causes the rotating mass 1604 to be selectively coupled to, and decoupled from, the output anvil 1622, and which increases the torque, transmitted to the output anvil 1622, by at least 30%.

In some implementations, when the electronic clutch 1612 is activated, the rotating mass 1604 (e.g., a high-speed flywheel) may be operatively coupled (e.g., directly coupled) to the carriage plate driver 1616, which results in a one to one coupling of the high speed flywheel to the output anvil. The inventors originally thought that coupling the high-speed flywheel through the gear box would multiply the output anvil torque by the gear ratio without any effect on the operator; however, it was unexpectedly discovered that this was not the case and in fact the gear ratio (if greater than 1:1) resulted in a significant torque coupled to the operator which was nearly equal to the gear ratio minus 1. As an example, if a 7:1 gear ratio was used to couple the flywheel, then the operator felt an increase of six times in the reactionary torque. Directly coupling the gear carrier 1618 to the output anvil 1622, and, therefore, directly coupling the carriage plate driver 1616 to the output anvil 1612, enables the gear ratio to be decreased from 7:1 to 1:1. This enables the rotating mass 1604 (e.g., the free spinning flywheel) to directly increase the torque on the output anvil 1622 with a minimal effect on the reactionary torque which turned into a huge benefit for the operator from a reactionary torque standpoint In some implementations, a one-way overrun bearing (e.g., the bypass shaft overrun bearing 1810 shown and described in connection with FIG. 3 and/or as described in more detail elsewhere herein) may be installed between the bypass shaft 1610 and a center drive (e.g., the center drive 1804 shown and described in connection with FIG. 3 and/or as described in more detail elsewhere herein) to reduce reactionary torque (e.g., internal reactionary torque) and potential associated wear of one or more components of the orthopedic rotary tool 1600 (e.g., which is dependent on a construction of the clutch being used by the orthopedic rotary tool 1600).

In some implementations, the activation of the electronic clutch 1612 may be associated with reducing the motor power and or speed by 10% or more such as to further decouple the reactionary torque communicated from the anvil to the operator or robot (it is understood that although the present disclosure refers to an operator, this function could be performed by a robot).

In some implementations, the electronic clutch 1612 may be activated in response to a 1% (or more) reduction of an output anvil rpm from the output anvil no-load rpm as detected by a sensor (e.g., the rotational speed sensor 1614). For example, if the output anvil no-load rpm is 300 rpm, then the electronic clutch 1612 may be activated in response to the sensor detecting an output anvil rpm of 299 (e.g., a 1% reduction in rpm from 300 rpm).

In some implementations, the decoupling of the motor 1624 (e.g., by disengaging or reducing the power to the motor 1624) reduces a passthrough torque (e.g., torque coupled from the output anvil 1622 back through to the motor 1624, a motor mount and a handpiece of the orthopedic rotary tool 1600). Furthermore, a rotational energy associated with the rotating mass 1604 increases by enabling access to the rotating inertia of the motor 1624.

In some implementations, an amount of time that the rotating mass 1604 is engaged, via the electronic clutch 1612 (e.g., via activation of the electronic clutch 1612), may be between a range (e.g., between approximately 2 milliseconds and 100 milliseconds or less than (or equal to) 50 milliseconds, among other examples). In some implementations, the rotating mass 1604 increases a peak output torque, as measured at the output anvil 1622, by (or at least by) 100% over a main drive axis (e.g., the first drive path through the bypass shaft 1610 as described in more detail elsewhere herein) for a period of at least 2 milliseconds.

In some implementations, the electronic clutch 1612 engages (e.g., activates) in less than (or equal to) twenty milliseconds, where engagement of the electronic clutch 1612 is defined as moving from 10% to 80% of transmitted torque through the electronic clutch 1612. The electronic clutch 1612 may be disengaged (e.g., may be deactivated) to allow the motor 1624 to drive reaccelerate the rotating mass 1604.

In some implementations, if the controller determines that the output speed (e.g., of the output anvil 1622) is in the desired output rpm range, then the controller enables the orthopedic rotary tool 1600 to function normally (e.g., the output anvil 1622 is driven by the bypass shaft 1610), and the electronic clutch 1612 is deactivated (e.g., which causes the rotating mass 1604 to be decoupled from the output anvil 1622). If the controller determines that the output speed (e.g., an output rotational speed of the output anvil 1622) drops below an output speed threshold, then the controller may activate and deactivate (e.g., in a pulsed manner) the electronic clutch 1612 to overcome the excessive load torque encountered by the output anvil 1622 and increase the output speed.

Figure 8:
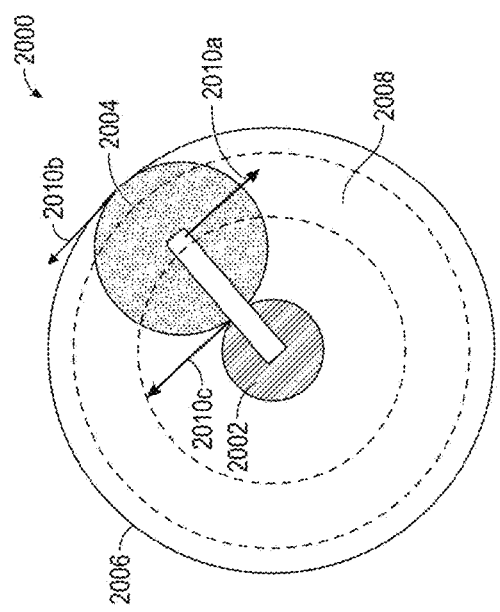
FIG. 8 is a diagram of an example driven sun gear for a planetary gear box.

FIG. 8 is a diagram of an example driven sun gear 2000 for a planetary gear box. As shown in FIG. 8, the driven sun gear includes a sun gear 2002, planet gear 2004, a ring gear 2006, and a gear carrier 2008. In some implementations, the planetary gearbox operates via a fixed ring gear, a driven sun gear, and planet gears rotating around the sun gear. The planet gears 2004 translate around the sun gear 2002 and drive the output through a gear carrier 2008. This configuration can create gear ratios from 3:1 to 10:1 or more. In this configuration, the input torque on the sun gear 2002 creates a reactionary force component on the ring gear 2006. Because the ring gear 2006 is rigidly fixed to the housing, this reactionary force is transferred to the operator of the orthopedic rotary tool. For example, in a driven sun gear scenario, a torque applied to a sun gear 2002 is communicated to a planet gear 2004. When a ring gear 2006 is added, the planet gear 2004 orbits around the sun gear 2002 and the carrier 2008 drives the output. The force vectors 2010a, 2010b, and 2010c are equal and opposite on the planet gear. The reactionary torque on the ring gear 2006 is $F_{planet}*Radius_{ring\ gear}$. It should be noted that, when using a planetary gear box, there are several configurations that may be used to deliver torque.

Figure 9:
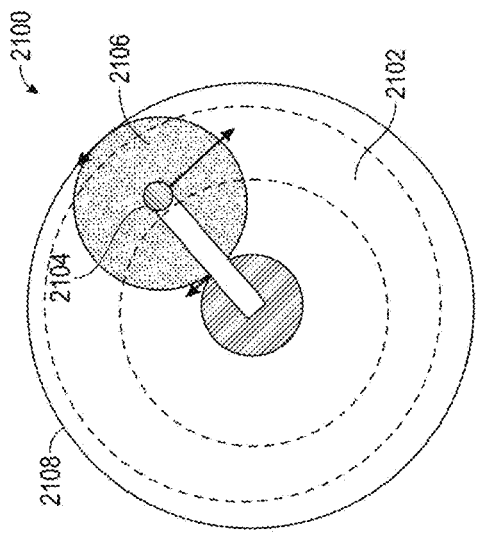
FIG. 9 is a diagram of an example driven gear carrier for a planetary gear box.

FIG. 9 is a diagram of an example driven gear carrier 2100 for a planetary gear box. As shown in FIG. 9, the driven sun gear 2100 includes a gear carrier 2102, a shaft 2104, a planet 2106, and a ring gear 2108. As another example, a fixed ring gear and a driven gear carrier may be utilized. The gear carrier 2102 is driven by shafts 2104 coupled to the carriage plate driver, bypassing the sun gear and planet gears 2106. In this example, the gear box behaves in a 1:1 gear ratio, allowing the reactionary torque to be carried by the shafts 2104 driving the gear carrier 2102, which transmits the torque directly back to the slip clutch and subsequently to the motor.

In a second scenario, for example, the carrier 2102 is driven solely by a shaft 2104 that is connecting to a rotating mass with a large kinetic energy. The direct coupling of the carrier 2102 to the shaft 2104 results in a 1:1 ratio. Because there is no mechanical advantage of the gears, the reactionary forces on the planet gear 2106 and ring gear 2108 become negligible. Accordingly, in some implementations, high energy rotational mass may be clutched through a 1:1 gear ratio, as described in more detail elsewhere herein. This helps explain the unexpected discovery that directly coupling the flywheel in a ratio of nearly 1:1 to the output resulted in minimal reactionary torque fed back to the operator.

With reference to FIGS. 1-4, using the magnetic slip clutch 1608 and the one way bearing 1810 on the bypass shaft 1610 greatly reduces contact wear between components. For example, an advantage of coupling the rotating mass 1604 through a 1:1 gear ratio on the secondary gearbox 1620 is that there will be no reactionary torque transmitted to the housing through the secondary gearbox ring gear. It is understood that coupling the electronic clutch 1612 to a 1:1 gear ratio is the same as (or similar to) coupling the electronic clutch 1612 directly to the output anvil 1622. The one way bearing 1810 may reduce the wear which would occur in a contacting slip clutch such as a ball cup spring relief clutch or a friction clutch. It is noted that the magnetic slip clutch 1608 can be used independently of the one way bearing 1810 on the bypass shaft 1610 (e.g., the magnetic slip clutch 1608 may be used without the one-way bearing).

Figure 10A:
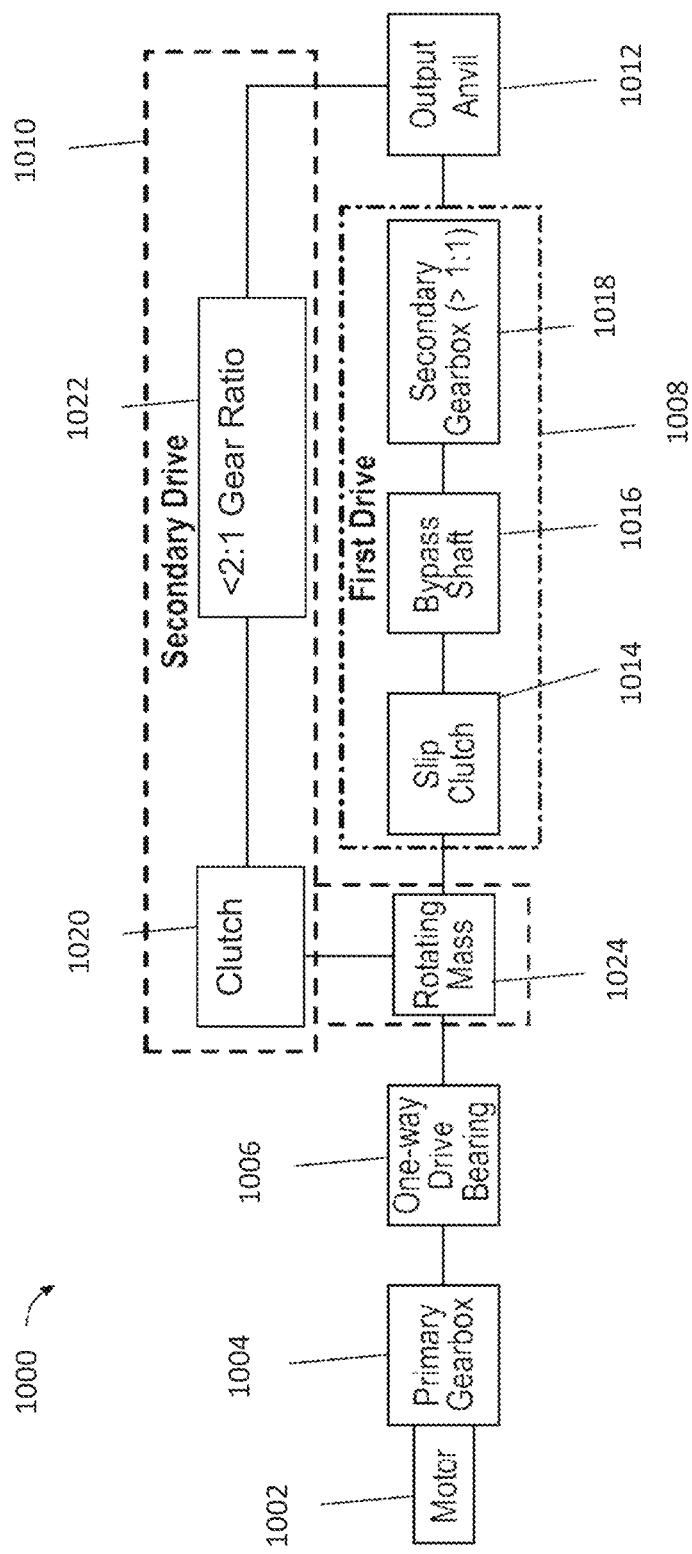
FIGS. 10A-10C are diagrams of example orthopedic rotary tools.
Figure 10B:
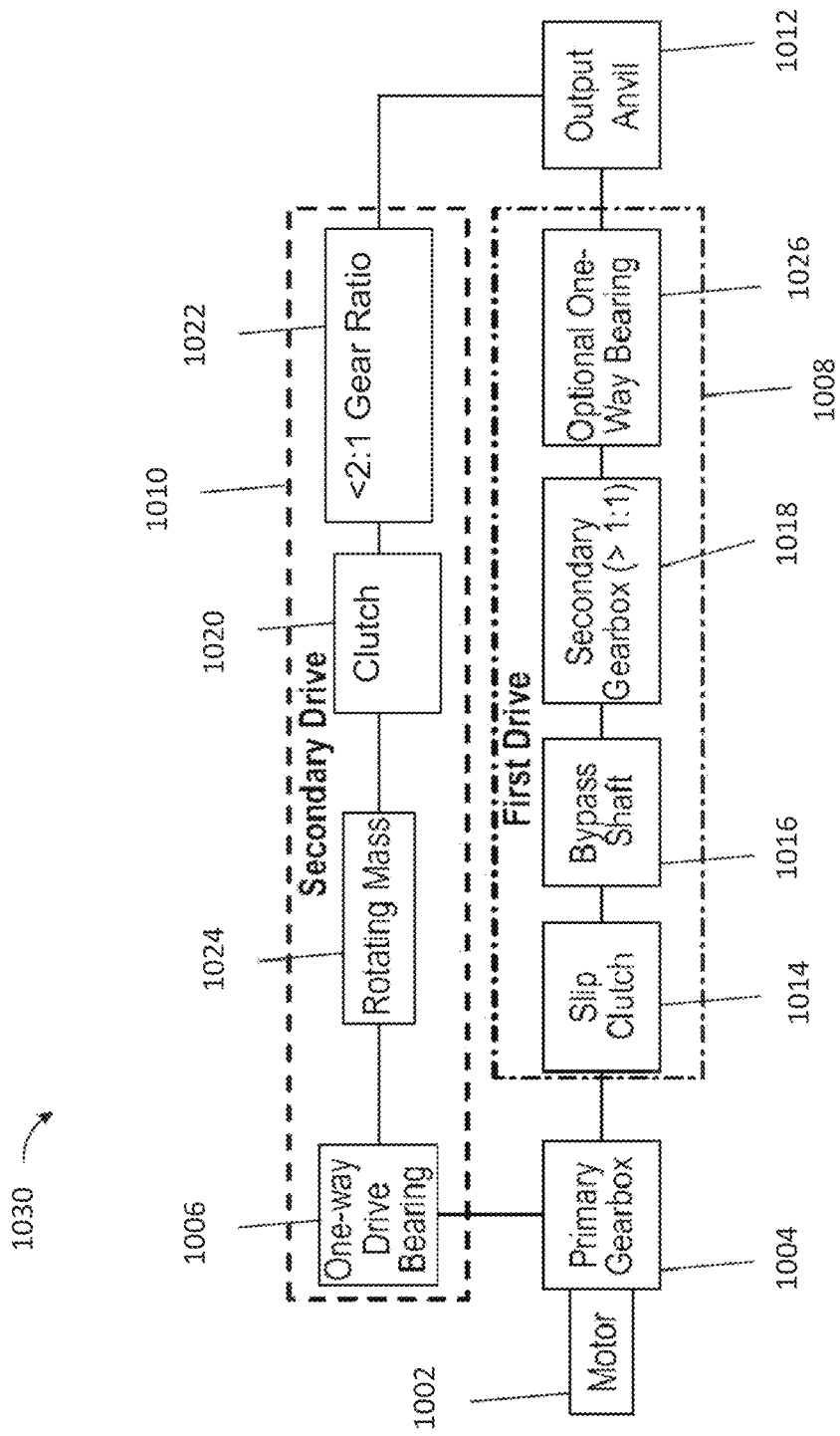
Figure 10C:
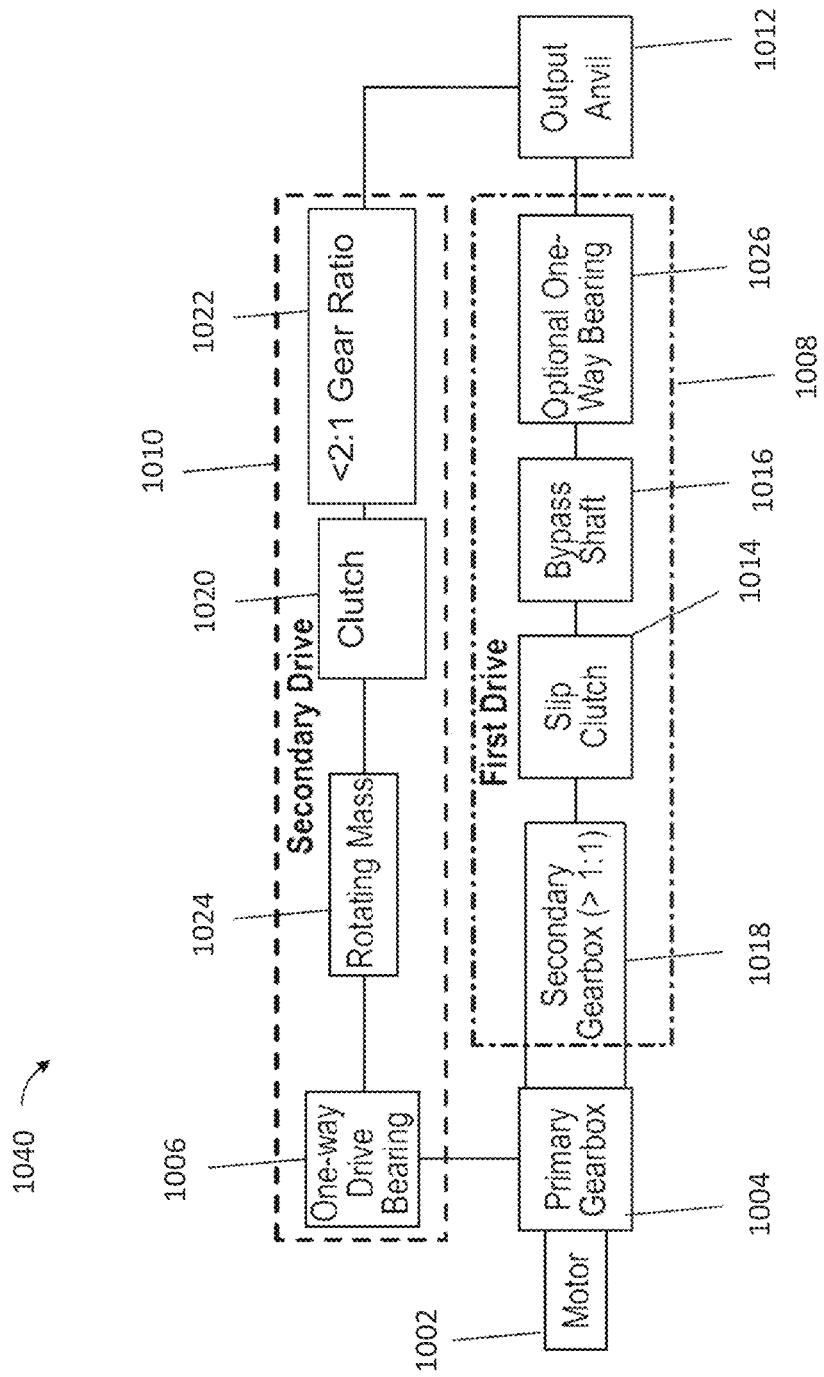

FIGS. 10A-10C are diagrams of example orthopedic rotary tools 1000, 1030, and 1040, respectively. Each of the orthopedic rotary tools 1000, 1030, and 1040 include a motor 1002, a primary gearbox 1004, a one-way drive bearing 1006 (which can be optional), a first drive 1008, a secondary drive 1010, an output anvil 1012, a slip clutch 1014, a bypass shaft 1016, a secondary gearbox 1018 (e.g., that has a greater than a 1:1 gear ratio), a clutch 1020, a gear ratio 1022 of less than 2:1, and a rotating mass 1024. As shown in FIG. 10A, the first drive 1008 includes the slip clutch 1014, the bypass shaft 1016, and the secondary gearbox 1018, and the secondary drive 1010 includes the clutch 1020, the gear ratio 1022, and the rotating mass 1024.

The motor 1002 of the orthopedic rotary tool 1030 of FIG. 10B drives the rotating mass 1024 and the slip clutch 1014 independently. The orthopedic rotary tool 1030 of FIG. 10B further includes an optional one-way drive bearing 1026 after the secondary gearbox 1018. The first drive 1008 includes the slip clutch 1014, the bypass shaft 1016, the secondary gearbox 1018, and the optional one-way bearing 1024. The secondary drive 1010 includes the one-way drive bearing 1006, the rotating mass 1024, the clutch 1020, and the gear ratio 1022.

The first drive 1008 and the secondary drive 1010 of the orthopedic rotary tool 1040 of FIG. 10C include the same components as FIG. 10B; however, the secondary gearbox 1018 of the orthopedic rotary tool 1040 of FIG. 10C is positioned between the primary gearbox 1004 and the slip clutch 1014.

As indicated above, FIGS. 10A-10C are provided as examples. Other examples may differ from what is described with regard to FIGS. 10A-10C. The number and arrangement of the various components shown in FIGS. 10A-10C are provided as examples. In practice, there may be additional components, fewer components, different components, or differently arranged components than those shown in FIGS. 10A-10C. Furthermore, components shown in FIGS. 10A-10C may be implemented within a single orthopedic rotary tool. Additionally, or alternatively, a set of components (e.g., one or more components) shown in FIGS. 10A-10C may perform one or more functions described as being performed by another set of components shown in FIGS. 10A-10C.

Figure 11:
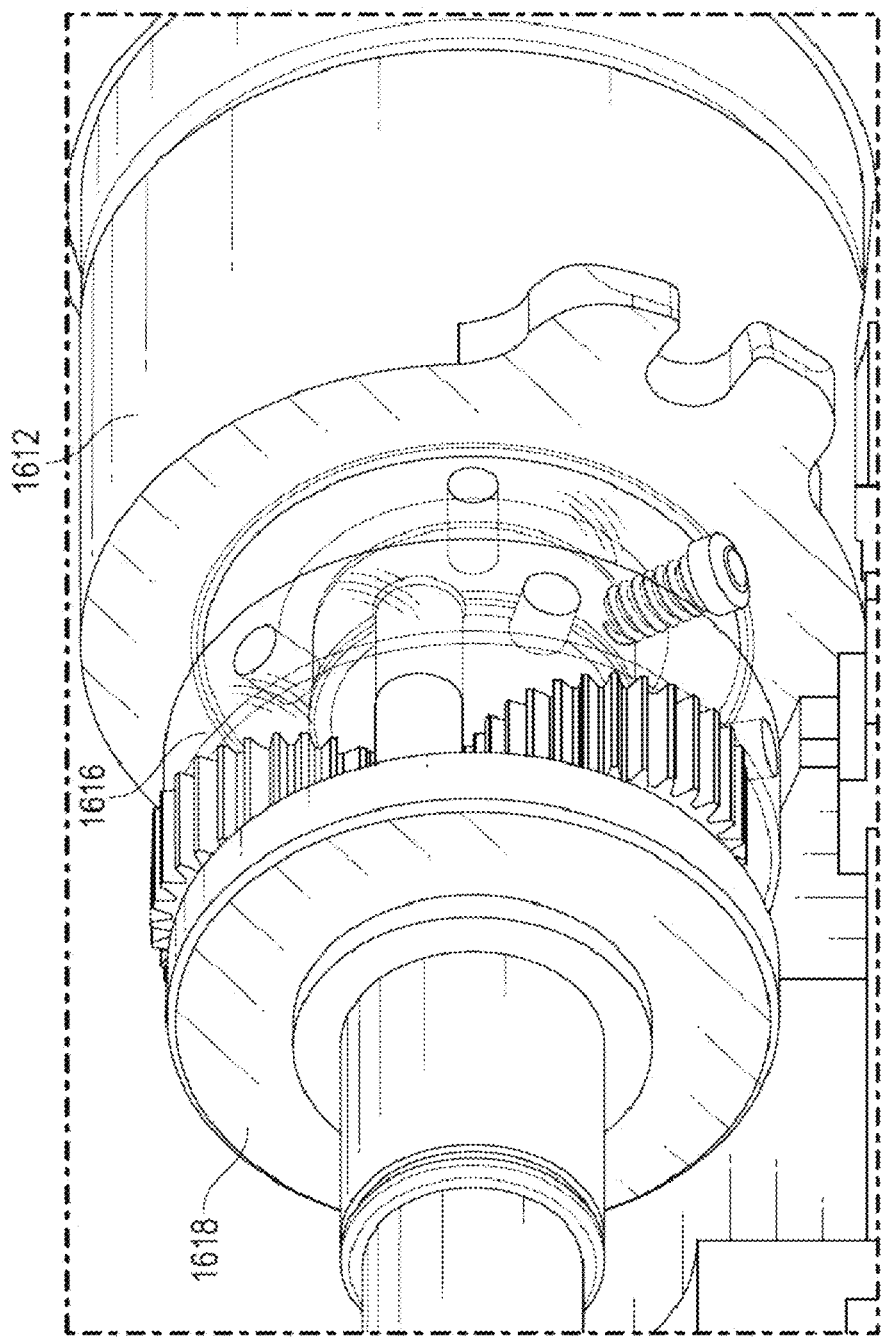
FIG. 11 is a partial diagram of the orthopedic rotary tool of FIG. 1.

FIG. 11 is partial diagram of an example of a direct coupling of the carriage plate driver 1616 to the output anvil 1622 via the gear carrier 1618 of the orthopedic rotary tool 1600 of FIG. 1, which enables a 1:1 gear ratio of the orthopedic rotary tool 1600.

Figure 12A:
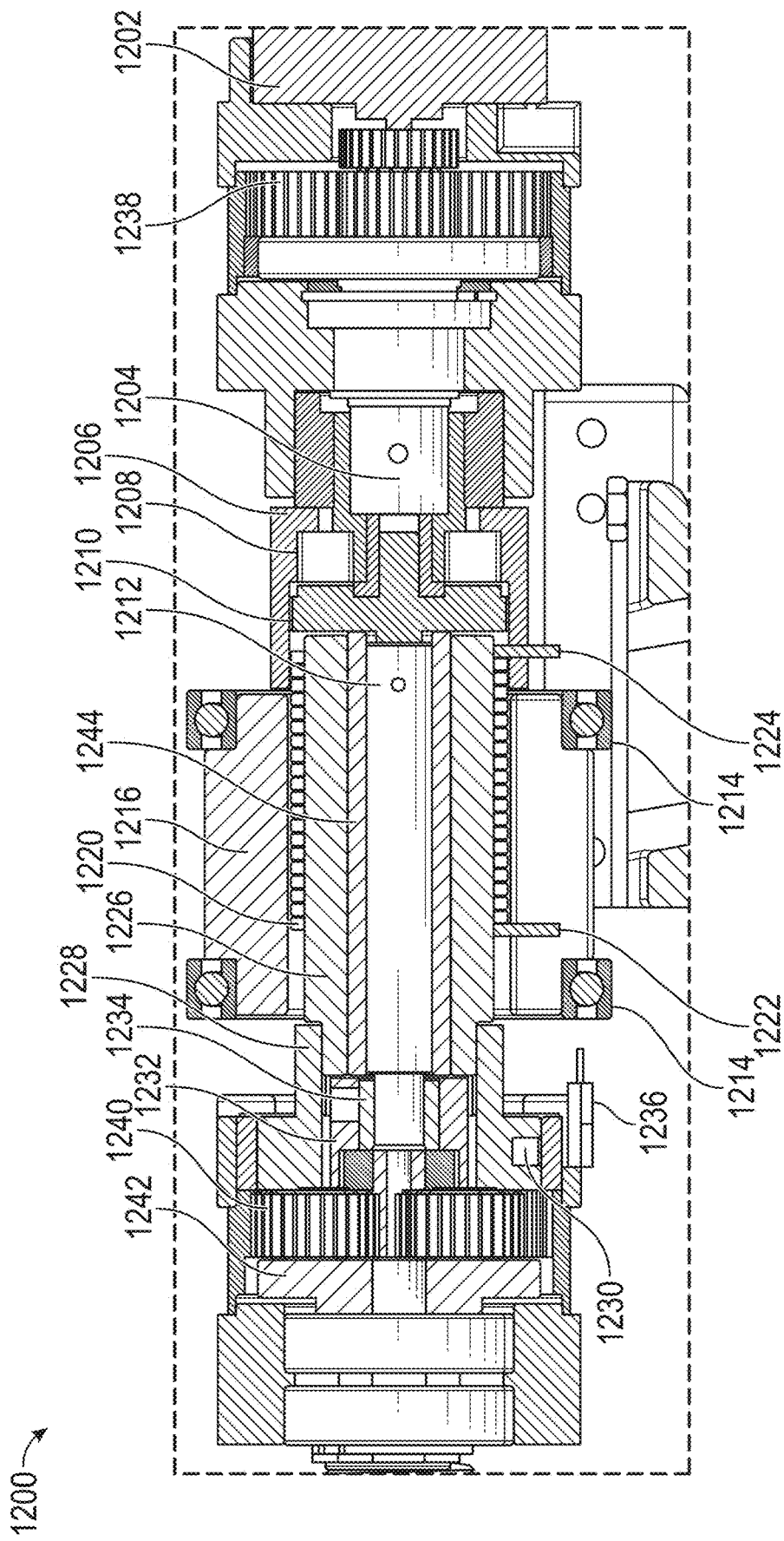
FIG. 12A is a diagram of an example orthopedic rotary tool.
Figure 12B:
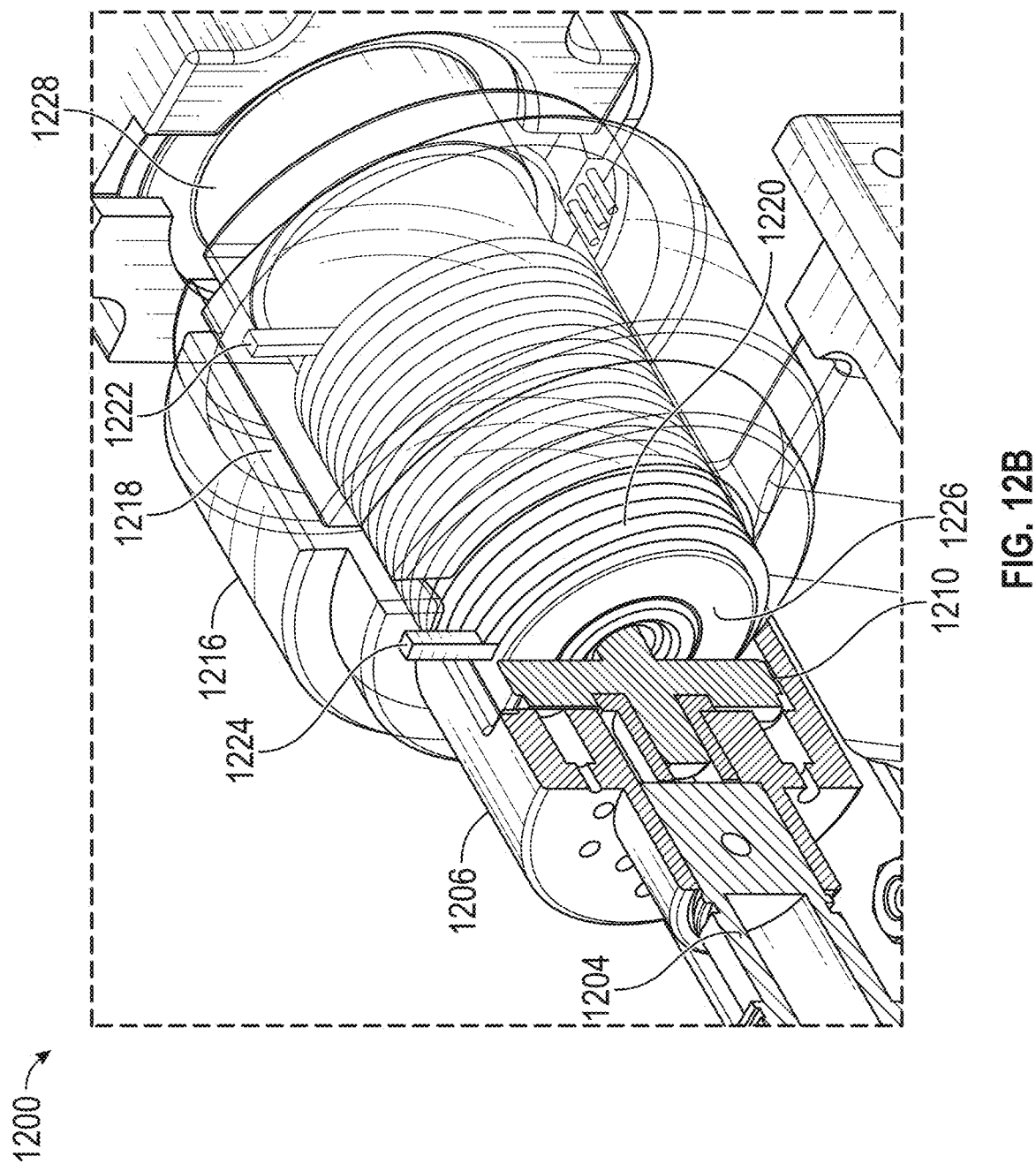
FIG. 12B is a partial diagrammatic cross-section of the orthopedic rotary tool of FIG. 12A.
Figure 12C:
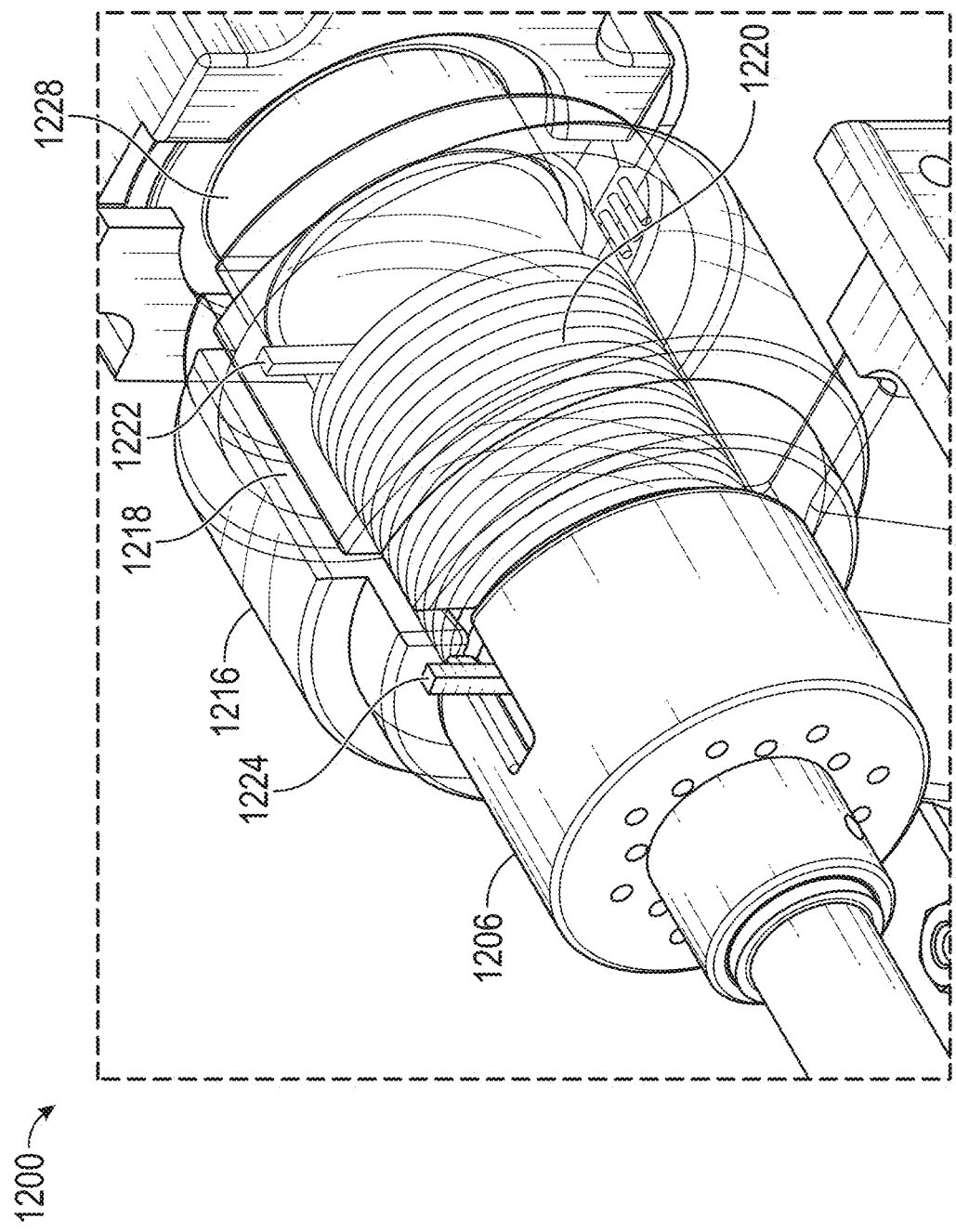
FIG. 12C is a partial diagram of the orthopedic rotary tool of FIG. 12A.

FIG. 12A is a diagram of an example orthopedic rotary tool 1200. FIGS. 12B-12C are partial diagrams of the orthopedic rotary tool 1200 of FIG. 12A. As shown in FIGS.

12A-12C, the orthopedic rotary tool 1200 includes a motor 1202, a drive shaft 1204, a clutch driver 1206 (e.g., a spring-trip slip-clutch driver (STSCD)), one or more magnets 1208 (e.g., one or more STSCD magnets), a bypass drive 1210, a bypass shaft 1212, ball bearings 1214, a flywheel 1216, flywheel slot 1218, a wrap spring 1220, a flywheel spring tang 1222, a control spring tang 1224, a wrap down hub 1226, a carriage plate driver 1228, carriage plate driver magnets 1230, a bypass pinion 1232, a one-way bearing 1234, an rpm sensor 1236, a primary gearbox 1238, secondary gearbox 1240, an output anvil 1242, and a bypass sleeve bushing 1244 (e.g., that enables relative motion between the bypass shaft 1212 and the wrap down hub 1226).

In some implementations, the orthopedic rotary tool 1200 may cause the output anvil 1242 to rotate using at least one of a first mode (e.g., associated with a first pathway) or a second mode (e.g., associated with a second pathway), as described in more detail elsewhere herein. As an example, when operating in the first mode, the orthopedic rotary tool 1200 may use the bypass drive 1210 to cause the output anvil 1242 to rotate. As another example, when operating in the second mode, the orthopedic rotary tool may use the flywheel 1216 to cause the output anvil 1242 to rotate.

In some implementations, an operator of the orthopedic rotary tool 1200 may cause the motor 1202 to rotate (e.g., by interacting with an operator interface of the orthopedic rotary tool 1200). The motor 1202 drives the draft shaft 1204, which, in turn, drives the clutch driver 1206 (e.g., the STSCD driver). When the orthopedic rotary tool 1200 operates in the first mode, the clutch driver 1206 drives the bypass drive 1210 through a slip clutch (e.g., a magnetic slip clutch). For example, the clutch driver 1206 may use the one or more magnets 1208 to drive the bypass drive 1210, which, in turn drives the bypass shaft 1212. The bypass shaft 1212 is operatively coupled to the bypass pinion 1232. The bypass drive 1210 and the bypass shaft 1212 may drive the bypass pinion 1232 through the one-way bearing 1234. The bypass pinion 1232 drives the output anvil 1242 through the secondary gearbox 1240.

In some implementations, when a load torque on the output anvil 1242 is higher than a slip torque (e.g., a slip torque associated with the clutch driver 1206, the one or more magnets 1208, and the bypass drive 1210), the bypass drive 1210 and the bypass shaft 1212 slip. This causes a rotational speed of the carriage plate driver 1228 to be reduced (e.g., the carriage plate driver 1228 will slow down or stop moving).

In some implementations, the carriage plate driver magnets 1230 may be disposed on the carriage plate driver 1228 (e.g., the carriage plate driver magnets 1230 may be regularly spaced on the carriage plate driver 1228). The rpm sensor 1236 may be positioned to detect movement of the carriage plate magnets 1230. The rpm sensor 1236 may detect a rotational speed of the carriage plate driver 1228 based on the movement of the carriage plate driver magnets 1230. The rpm sensor 1236 may send, and a controller (e.g., associated with a control board) may receive, an indication of the rotational speed of the carriage plate driver 1228. The controller may activate, based on determining that the rotational speed of the carriage plate driver 1228 satisfies (e.g., has dropped below) a rotational speed threshold, the second mode (e.g., the controller may cause the orthopedic rotary tool 1200 to operate in the second mode by engaging the flywheel 1216).

As an example, the orthopedic rotary tool 1200 may drive the clutch driver 1206 which, in turn, drives the wrap spring 1220 through the flywheel spring tang 1222 and the control spring tang 1224. The flywheel spring tang 1222 may be aligned within the flywheel slot 1218 and the control spring tang 1224 may be aligned within a slot of the clutch driver 1206. As the clutch driver 1206 drives the control spring tang 1224 in a first direction, the control spring tang 1224 generates a radial force that unwinds coils of the wrap spring 1220 (e.g., the wrap spring 1220 expands). In other words, the control spring tang 1224 may cause the wrap spring 1220 to partially unwind when the control spring tang 1224 is driven in the first direction. In this way, because the wrap spring 1220 unwinds when the orthopedic rotary tool 1200 operates in the first mode (e.g., using the bypass drive 1210 and the bypass shaft 1212 to rotate the control spring tang 1224 in the first direction), the wrap spring 1220 does not interact with the wrap down hub 1226 during operation of the orthopedic rotary tool 1200 in the first mode.

Additionally, as the clutch driver 1206 drives the control spring tang 1224 in the first direction, the control spring tang 1224 causes the flywheel 1216 to rotate (e.g., accelerate) in the first direction, which enables the flywheel 1216 to generate and store the rotational kinetic energy (e.g., the flywheel 1216 may interact with ball bearings to rotate at a high speed with minimal friction).

In some implementations, the controller may activate the second mode (e.g., the controller may cause the orthopedic rotary tool 1200 to operate in the second mode by engaging the flywheel 1216) based on determining that the rotational speed of the carriage plate driver 1228 satisfies (e.g., has dropped below) the rotational speed threshold. As an example, if the output anvil 1242 encounters an excessive load torque, then a rotational speed of the carriage plate driver 1228 will reduce (e.g., because of slippage associated with the bypass drive 1210 and the bypass shaft 1212) and the controller may cause the orthopedic rotary tool 1200 to operate in the second mode to overcome the excessive load torque.

In some implementations, to operate in the second mode, the controller may reduce a rotational speed of the clutch driver 1206 (e.g., by causing a rotational speed of the motor 1202 to be reduced), which causes a rotational speed of the control spring tang 1224 to be reduced. In response to the rotational speed of the control spring tang 1224 being reduced, the flywheel 1216 will continue to rotate due to its high rotational inertia. The flywheel 1216 drives the flywheel spring tang 1222, and the flywheel spring tang 1222 winds the coils of the wrap spring 1220 (e.g., the wrap spring 1220 contracts) to operatively couple the wrap spring 1220 to the wrap down hub 1226. In other words, the flywheel spring tang 1222 may cause the wrap spring 1220 to operatively couple to the wrap down hub 1226. This results in the flywheel 1216 being operatively coupled to the output anvil 1242 (e.g., via the wrap spring 1220 and the wrap down hub 1226) in an approximate 1:1 gear ratio. In this way, when operating in the second mode, the flywheel 1216 applies a high rotary energy pulse to the output anvil 1242 to overcome the excessive torque load. After the high energy pulse has been applied to the output anvil, the controller can increase the rotational speed of the motor which releases the wrap spring 1220 from the wrap down hub 1226 and accelerates the flywheel (e.g., associated with the first mode of operation). The rpm sensor 1236 indicates to the controller when to shift between first mode and second mode continuously throughout the operational cycle of the tool.

Figure 13:
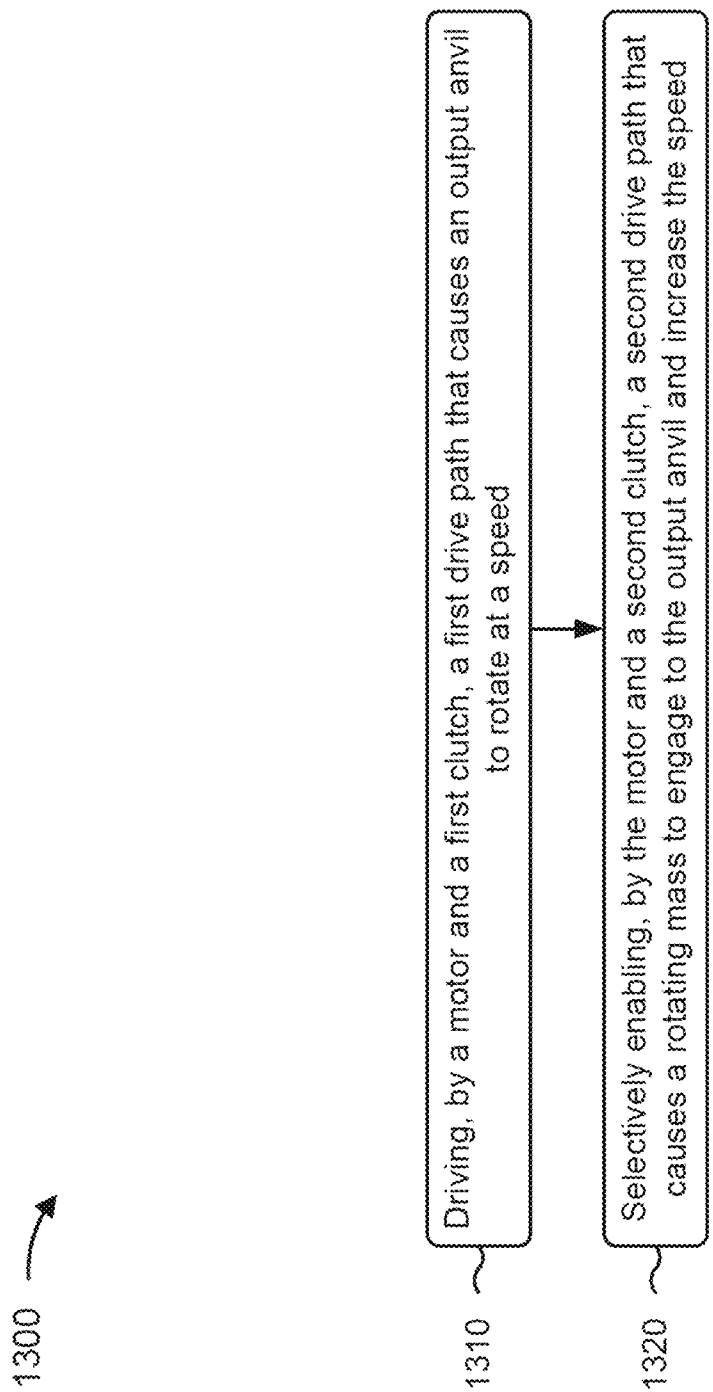
FIG. 13 is a flowchart of an example process associated with operating an orthopedic rotary tool, in accordance with some embodiments of the present disclosure.

FIG. 13 is a flowchart of an example process 1300 associated with operating an orthopedic rotary tool. As shown in FIG. 13, process 1300 may include driving, by a motor and a first clutch, a first drive path that causes an output anvil to rotate at a speed (block 1310). As an example, process 1300 may include driving, by the motor and the first clutch, the first drive path that causes the output anvil to rotate at the speed, as described in more detail elsewhere herein. As further shown in FIG. 13, process 1300 may include selectively enabling, by the motor and a second clutch, a second drive path that causes a rotating mass to engage the output anvil and increase the speed (block 1320). As an example, process 1300 may include selectively enabling, by the motor and the second clutch, the second drive path that causes the rotating mass to engage the output anvil and increase the speed, as described in more detail elsewhere herein.

In some implementations, the second drive path may be selectively enabled when the speed of the output anvil drops to less than a percentage of a design speed (e.g., less than 99% of the design speed). In some implementations, the first clutch may be a slip clutch and the second drive path may be selectively enabled when the slip clutch begins slipping. In some implementations, the second drive path may be selectively enabled based on at least one of a duty cycle or a frequency. In some implementation, selectively enabling the second drive path may causes an output torque at the anvil to increase by at least 30%. In some implementations, the engagement of the rotating mass to the output anvil may counteract a load torque received at the output anvil. In some implementations, the load torque may be at least one of approximately 2 to 50 inch-pounds.

Although FIG. 13 shows example blocks of process 1300, in some implementations, process 1300 may include additional blocks, fewer blocks, different blocks, or differently arranged blocks than those depicted in FIG. 13. Additionally, or alternatively, two or more of the blocks of process 1300 may be performed in parallel. The process 1300 is an example of one process that may be performed by one or more devices described herein. These one or more devices may perform one or more other processes based on operations described herein, such as the operations described in connection with FIGS. 1-13. Moreover, while the process 1300 has been described in relation to the devices and components of the preceding figures, the process 1300 can be performed using alternative, additional, or fewer devices and/or components. Thus, the process 1300 is not limited to being performed with the example devices, components, hardware, and software explicitly enumerated in the preceding figures.

As used herein, the term "component" is intended to be broadly construed as hardware, firmware, or a combination of hardware and software. It will be apparent that systems and/or methods described herein may be implemented in different forms of hardware, firmware, and/or a combination of hardware and software. The actual specialized control hardware or software code used to implement these systems and/or methods is not limiting of the implementations. Thus, the operation and behavior of the systems and/or methods are described herein without reference to specific software code—it being understood that software and hardware can be used to implement the systems and/or methods based on the description herein.

As used herein, satisfying a threshold may, depending on the context, refer to a value being greater than the threshold, greater than or equal to the threshold, less than the threshold, less than or equal to the threshold, equal to the threshold, not equal to the threshold, or the like.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set. As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiple of the same item.

When "a processor" or "one or more processors" (or another device or component, such as "a controller" or "one or more controllers") is described or claimed (within a single claim or across multiple claims) as performing multiple operations or being configured to perform multiple operations, this language is intended to broadly cover a variety of processor architectures and environments. For example, unless explicitly claimed otherwise (e.g., via the use of "first processor" and "second processor" or other language that differentiates processors in the claims), this language is intended to cover a single processor performing or being configured to perform all of the operations, a group of processors collectively performing or being configured to perform all of the operations, a first processor performing or being configured to perform a first operation and a second processor performing or being configured to perform a second operation, or any combination of processors performing or being configured to perform the operations. For example, when a claim has the form "one or more processors configured to: perform X; perform Y; and perform Z," that claim should be interpreted to mean "one or more processors configured to perform X; one or more (possibly different) processors configured to perform Y; and one or more (also possibly different) processors configured to perform Z."

No element, act, or instruction used herein should be construed as critical or essential unless explicitly described as such. Also, as used herein, the articles "a" and "an" are intended to include one or more items and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, or a combination of related and unrelated items), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

In the preceding specification, various example embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

What is claimed is:

1. An orthopedic rotary tool, comprising:
   a motor;
   a drive shaft operatively coupled to the motor;
   an output anvil operatively coupled to the drive shaft;
   a rotating mass;
   a clutch operatively coupled to the rotating mass and the anvil,
      wherein the clutch is configured to engage the rotating mass to the output anvil when the output anvil drops to less than a design speed, and
      wherein after such engagement the clutch is configured to disengage the rotating mass from the output anvil to allow the rotating mass to reaccelerate; and
   a controller configured to:
      cause the clutch to selectively couple the rotating mass to the output anvil at a frequency consistent with maintaining an output anvil rpm of less than 500 rpm.

2. The orthopedic rotary tool of claim 1, wherein the controller is further configured to:
   cause the clutch to selectively engage and disengage the rotating mass to the output anvil based on at least one of:
      a duty cycle,
      a frequency, or
      a deviation in a speed of the output anvil from the design speed.

3. The orthopedic rotary tool of claim 1, wherein the controller is further configured to:
   deactivate the motor for at least a portion of a time during which the clutch is coupling the rotating mass to the output anvil.

4. The orthopedic rotary tool of claim 1, wherein the rotating mass communicates to the anvil at a gear ratio of between 0.7 to 1.5.

5. The orthopedic rotary tool of claim 1, wherein the controller is further configured to:
   deactivate the motor for at least a portion of a time during which the clutch is coupling the rotating mass to the output anvil.

6. The orthopedic rotary tool of claim 1, further comprising:
   a one-way drive bearing operatively coupled to the rotating mass,
      wherein the motor is configured to drive the rotating mass via the one-way bearing to generate rotational kinetic energy that is stored by the rotating mass.

7. The orthopedic rotary tool of claim 1, further comprising:
   a second clutch that couples the motor, the drive shaft, and the output anvil,
      wherein the second clutch is at least one of:
         a one-way clutch,
         a slip-clutch, or
         a break-away clutch.

8. The orthopedic rotary tool of claim 1, wherein the drive shaft is operably connected to the motor via a second clutch.

9. The orthopedic rotary tool of claim 1, further comprising:
   a controller configured to:
      cause the clutch to selectively engage and disengage the rotating mass to the output anvil based on at least one of:
         a duty cycle,
         a frequency, or
         a deviation in a speed of the output anvil from the design speed.

10. An orthopedic rotary tool, comprising:
    a motor;
    a first drive path;
    a first clutch;
    a second drive path;
    a second clutch; and
    an output anvil;
       wherein the motor is configured to drive the first drive path and the second drive path,
       wherein the first drive path is configured to drive the output anvil through the first clutch, and
       wherein the second drive path is configured to be selectively enabled through the second clutch.

11. The orthopedic rotary tool of claim 10, further comprising:
    a rotating mass; and
    wherein the second clutch selectively couples the rotating mass to the output anvil based on a reduction in a speed of the output anvil of at least 20% when driven solely by the first drive path.

12. The orthopedic rotary tool of claim 11, further comprising:
    a one-way bearing that operatively couples the motor to the rotating mass; and
    a controller configured to:
       deactivate the motor based on causing the second clutch to selectively couple the rotating mass to the output anvil.

13. The orthopedic rotary tool of claim 11, wherein selectively coupling the rotating mass to the output anvil causes a speed of the output anvil to increase.

14. An orthopedic rotary tool, comprising:
    a motor;
    a drive shaft operatively coupled to the motor;
    an output anvil operatively coupled to the drive shaft;
    a rotating mass;
    a clutch operatively coupled to the rotating mass and the anvil,
       wherein the clutch is configured to engage the rotating mass to the output anvil when the output anvil drops to less than a design speed, and
       wherein after such engagement the clutch is configured to disengage the rotating mass from the output anvil to allow the rotating mass to reaccelerate; and
    a controller configured to:
       cause the clutch to selectively couple the rotating mass to the output anvil shaft at a frequency of at least five hertz for part of an operation.

15. The orthopedic rotary tool of claim 14, wherein the rotating mass communicates to the anvil at a gear ratio of between 0.7 to 1.5.

16. The orthopedic rotary tool of claim 14, further comprising:
    a controller configured to:
       deactivate the motor for at least a portion of a time during which the clutch is coupling the rotating mass to the output anvil.

17. The orthopedic rotary tool of claim 14, further comprising:
    a one-way drive bearing operatively coupled to the rotating mass,
       wherein the motor is configured to drive the rotating mass via the one-way bearing to generate rotational kinetic energy that is stored by the rotating mass.

18. The orthopedic rotary tool of claim 14, further comprising:
- a second clutch that couples the motor, the drive shaft, and the output anvil,
  - wherein the second clutch is at least one of:
    - a one-way clutch,
    - a slip-clutch, or
    - a break-away clutch.

19. The orthopedic rotary tool of claim 14, wherein the drive shaft is operably connected to the motor via a second clutch.

20. The orthopedic rotary tool of claim 14, wherein the controller is further configured to:
- cause the clutch to cause the clutch to selectively couple the rotating mass to the output anvil at a frequency consistent with maintaining an output anvil rpm of less than 500 rpm.

* * * * *